United States Patent
Karlsson (10) Patent No.: US 11,229,421 B2
(45) Date of Patent: Jan. 25, 2022

(54) METHOD AND DEVICE FOR THE COLLECTION OF ORAL FLUIDS

(71) Applicant: KARLSSON & NOVAK MEDICAL AB, Umeå (SE)

(72) Inventor: Roger Karlsson, Umeå (SE)

(73) Assignee: KARLSSON & NOVAK MEDICAL AB, Umea (SE)

(*) Notice: Subject to any disclaimer, the term of this patent is extended or adjusted under 35 U.S.C. 154(b) by 359 days.

(21) Appl. No.: 15/998,563

(22) Filed: Aug. 17, 2018

(65) Prior Publication Data

US 2019/0076131 A1 Mar. 14, 2019

Related U.S. Application Data

(63) Continuation of application No. PCT/SE2017/050139, filed on Feb. 14, 2017.

(30) Foreign Application Priority Data

Feb. 15, 2016 (SE) .................................. 1650195-9

(51) Int. Cl.
  *A61B 10/00* (2006.01)
  *A61J 17/00* (2006.01)

(52) U.S. Cl.
  CPC ...... *A61B 10/0051* (2013.01); *A61B 10/0096* (2013.01); *A61J 17/001* (2015.05); *A61B 2010/0006* (2013.01)

(58) Field of Classification Search
  CPC ...................... A61B 10/0051; A61B 10/0096
  See application file for complete search history.

(56) References Cited

U.S. PATENT DOCUMENTS

| | | | |
|---|---|---|---|
| 5,910,122 A | 6/1999 | D'Angelo | |
| 6,022,326 A | 2/2000 | Tatum et al. | |
| 2003/0220601 A1 | 11/2003 | Toomey | |
| 2009/0024058 A1 | 1/2009 | Blowick | |
| 2012/0046574 A1 | 2/2012 | Skakoon | |
| 2012/0095369 A1 | 2/2012 | Teixeira | |
| 2013/0116599 A1 | 5/2013 | Bullington | |
| 2015/0133817 A1 | 5/2015 | Slowey | |
| 2015/0246352 A1 | 9/2015 | Bullington | |
| 2016/0133817 A1 | 5/2016 | Makansi et al. | |

FOREIGN PATENT DOCUMENTS

| | | | |
|---|---|---|---|
| CN | 204484173 U | 7/2015 | |
| CN | 204971357 U | 1/2016 | |
| CN | 205072904 U | 3/2016 | |
| GB | 2484805 A | 4/2012 | |
| WO | WO-9720502 A1 * | 6/1997 | ......... A61B 10/0051 |

* cited by examiner

*Primary Examiner* — Christine H Matthews
(74) *Attorney, Agent, or Firm* — Gabriela B. Tomescu, Esq.; Bergenstråhle & Partners AB

(57) ABSTRACT

The present invention relates to a method and device for collection of oral fluids comprising the use of a sealed evacuated sample container.

19 Claims, 8 Drawing Sheets

METHOD AND DEVICE FOR THE COLLECTION OF ORAL FLUIDS

This application is the continuation of International Application No. PCT/SE2017/050139, filed 14 Feb. 2017, which claims the benefit of Swedish Patent Application No. SE 1650195-9, filed 15 Feb. 2016, the entire contents of which are hereby incorporated by reference.

The present invention relates to a method and device for the collection and optional evaluation of oral fluids.

BACKGROUND

There is an incentive to replace, where possible, invasive blood testing with non-invasive saliva testing due to several reasons including convenience and cost. Non-invasive test are a prerequisite for conducting body fluid analysis test away from professional health provides. Also, a significant part of the population experience pronounced needle aversion, specifically infants, children and to an extent also elderly. The risk of infection is also mitigated by the replacement of invasive blood testing with saliva testing. A skilled person (nurse) must typically be present when performing an invasive blood test adding complexity and cost compared to non-invasive saliva testing.

For the reasons mentioned above there is an impetus for an increased number of regulatory approved saliva testing protocols in the future.

The present invention provides a convenient device for the collection and optional evaluation of oral fluids. The device is designed to be fully integrated with standardized evacuated fluid sample vials.

GB 2484805 discloses an assembly for the collection and testing of oral fluids, e.g. saliva.

US 2012/0095369 A1 relates to a device for sampling body fluids.

US 2016/0133817 A1 discloses a saliva collection system comprising a pacifier portion, a stiffener, a collector and a pad compression tube. This concept is based on collecting saliva with an absorbent pad. Absorbed saliva is separated from the pad by compression. There is no teaching suggesting that saliva be collected by using an evacuated sample vial.

U.S. Pat. No. 5,910,122 discloses a method for saliva collection where saliva is collected by placing a sponge in the oral cavity. Saliva is absorbed into the sponge and separated from sponge by a pipette. The method and device in U.S. Pat. No. 5,910,122 is not adaptable for the accommodation of evacuated sealed sample vials.

WO 9720502 relates to a pacifier for the collection of saliva comprising an absorbent. The saliva needs in a further stage be separated from the absorbent.

SUMMARY

In general, the present invention relates to a method and device suitable for the collection and optional testing of oral fluids, e.g. saliva, using a sealed evacuated sample container (5). The vacuum or sub-atmospheric pressure present in the sealed evacuated sample container, once the seal is broken, is used for transferring oral fluids accumulated in an intra oral member (11), e.g. the flexible part of a pacifier, into the sample container (5). Hence, the sealed evacuated sample container provides at least two properties, transportation of oral fluids and storage.

INVENTION

The invention relates to a method and device as specified by the claims.

More specifically, the present invention relates to a method for collecting oral fluids where a sealed evacuated sample container (5) is applied for the transferal and optional storage of oral fluids from a flexible intra oral member (11) forming part of a collecting member (1). The flexible intra oral member (11) is placed into the oral cavity. As the flexible intra oral member (11) has at least one opening (13) oral fluids will be accumulated within the flexible intra oral member (11) as a reduced pressure is obtained by actuation of the flexible intra oral member (11). In order to sufficiently fill the flexible intra oral member (11) with oral fluids it is important that a reduced pressure can build up in the volume restricted by the flexible intra oral member and any part other part of the device outside the oral cavity, e.g. the rigid member (12) of the collecting member (1). For obtaining such a reduced pressure it is important that any part of the device outside the oral cavity restricting the volume for collection of oral fluids, e.g. the rigid member, is sealed. The above explanation is the reason that according to an embodiment the collecting member (1) is configured such that a pressure inside the flexible intra oral member (11) when present in the oral cavity is provided which enables the collection of oral fluids within the flexible intra oral member (11). The feature enabling the provision of reduced pressure inside the flexible oral member is that any structure of the collecting member enabling the transfer of oral liquid inside the flexible oral member is sealed. Seals of the collecting member (1) are exemplified in FIGS. 1 and 2, numbers 17 and 18. The seals (17 and 18 in FIGS. 1 and 2) enable the provision of a reduced pressure within the volume restricted by the flexible intra oral member (11) and the rigid member (12) of the collecting member (1).

According to the claims, the method provides for collecting oral fluids comprises the provision of: at least a collecting member (1) configured for the collection of oral fluids when present in an oral cavity, comprising a flexible intra oral member (11) and a rigid member (12), the flexible intra oral member (11) comprising at least one opening; and a sealed evacuated sample container (5), the method comprising placement of the flexible intra oral member (11) in the oral cavity, collection of the oral fluids in the flexible intra oral member (11), transferal of at least part of the oral fluid from the flexible intra oral member (11) into the sample container (5) by activation of the sub-atmospheric pressure of the evacuated sample container (5).

An important part of the method and some of the devices is the sealed evacuated sample container (5). For embodiments of the device not including a sealed evacuated sample container (5), an important feature is the presence of either a rigid member (12) or a guiding member (3) both configured for accommodating an a sealed evacuated sample container (5), more specifically configured for accommodating an axial movement of a sealed evacuated sample container (5).

As presented above, the transfer of the oral fluid is activated when the seal of the evacuated sample container (5) is penetrated. Hence, the sealed sample container (5) is typically activated when sufficient oral fluids are collected inside the collecting member (1). The seal of the sample container (5) can be activated by any suitable means capable of penetrating a seal. Preferably, the activation is executed by a rigid, hollow structure capable of breaking or penetrating the seal of the sample container (5) and/or or any other seal such as any seal present on the collecting member (1) or the coupling member (2). The rigid and hollow structure is typically incorporated with the collecting member (1), preferably the rigid member (12) of the collecting member (1). If the device also comprises a sealed coupling member (2), said coupling member also comprises a means (22) for penetrating the seal of the sealed evacuated sample container (5).

The invention further encompasses a device configured for the collection of oral fluids and the application of the device in the method for collecting oral fluids.

Without limiting the gist of the invention the device is defined according to the following embodiments:

I) A device configured for the collection of oral fluids comprising at least: a collecting member (1) comprising a flexible intra oral member (11) and a rigid member (12), the flexible intra oral member (11) comprising at least one opening (13), the rigid member configured to accommodate an axial movement of a sealed evacuated sample container (5), the collecting member being configured such that a pressure inside the flexible intra oral member (11) when present in the oral cavity is provided which enables the collection of oral fluids within the flexible intra oral member (11) and the collecting member (1) comprises means for penetration of the seal of the sealed evacuated sample container (5). The embodiment is exemplified by FIG. 9, (X1) and FIG. 8, (Y) where (3) is integrated into (12).

II) A device configured for the collection of oral fluids comprising at least: a collecting member (1) comprising a flexible intra oral member (11) and a rigid member (12), the flexible intra oral member (11) comprising at least one opening; a guiding member (3) configured for accommodating an axial movement of a sealed evacuated sample container (5), the guiding member (3) configured for enabling removable attachment to the rigid member (12) of the collecting member (1); where the collecting member is configured such that a pressure inside the flexible intra oral member (11) when present in the oral cavity is provided which enables the collection of oral fluids within the flexible intra oral member (11) and the collecting member comprises means for penetration of the seal of the sealed evacuated sample container (5). The embodiment is exemplified by FIG. 8, (X) and (Y), where in (Y) the device contains the individual part of a guiding member (3) and an rigid member (12) not including the part accommodating the sealed evacuated sample compartment (3); and FIG. 9 (X2), (Y)

Figure 7:
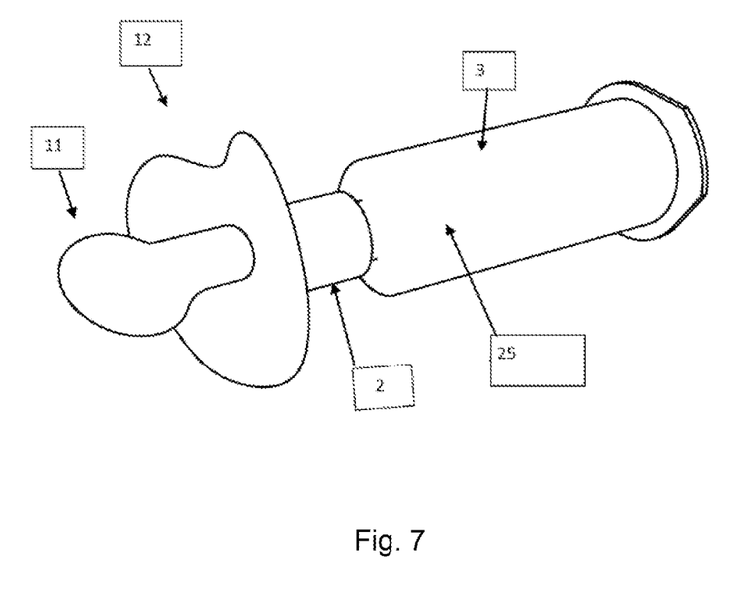
FIG. 7 shows a picture of a version of the concept according to embodiment III without sealed evacuated sample container.

III) A device configured for the collection of oral fluids comprising at least: a collecting member (1) comprising a flexible intra oral member (11) and a rigid member (12), the flexible intra oral member (11) comprising at least one opening; a sealed coupling member (2) comprising an internal volume (21) and means for penetrating a seal of a sealed evacuated sample container (5); a guiding member (3) configured for accommodating an axial movement of the sealed evacuated sample container (5); where the sealed coupling member (2) is configured for enabling removable attachment to the rigid member (12) of the collecting member (1), the guiding member (3) is configured for enabling removable attachment to the sealed coupling member (2), the collecting member being configured such that a pressure inside the flexible intra oral member (11) when present in the oral cavity is provided which enables the collection of oral fluids within the flexible intra oral member (11) and the collecting member comprises means for penetration of the seal of the sealed coupling member (2). FIG. 7 is an example of embodiment III.

It should be understood that the designs presented by the figures are non-limiting examples of disclosed embodiments.

By collecting member (1) is meant any structure which is suitable to be placed in an oral cavity for a period of time for the provision of a sufficient volume of oral fluids. The collecting member (1) typically comprises a flexible intra oral member (11) and a rigid member (12).

Common to all embodiments of the device is the presence of a structure enabling the accommodation of a sealed evacuated sample container (5) and the axial movement of said sample container. Said structure is, dependent on the embodiment, referred to as either collecting member (1), rigid member (12) or guiding member (3). The structure enabling the accommodation of a sealed evacuated sample container (5) may be integrated in the collecting member (1) and more specifically integrated into the rigid member (12) of the collecting member (1). Moreover, the collecting member is characterized as being configured such that a pressure inside the flexible intra oral member (11) when present in the oral cavity is provided which enables the collection of oral fluids within the flexible intra oral member (11) and comprising means (14) for penetration of the seal of the sealed evacuated sample container (5).

Before the sealed evacuated sample container is activated, i.e. the seal is penetrated (broken) it is advantageous if the device is positioned such that essentially oral fluids and not air is sucked into the sample container. Hence, after collection of the oral fluids in the collecting member and suitable after attachment of any individual parts of the device, the device is positioned such that the means for penetration is essentially vertical with the sample container at the 'lowest' position and the collecting member at the top.

According to an aspect the device, such as the devices according to embodiments I, II and III, may also comprise a sealed evacuated sample container (5).

According to a further aspect the device is provided in parts, such parts constituting a collecting member (1), and where appropriate a guiding member (3) and optionally a sealed coupling member (2). The individual parts are configured such that the parts can be easily attached to each other. Suitable means for attaching any of the parts are treads (23, 16).

Figure 4:
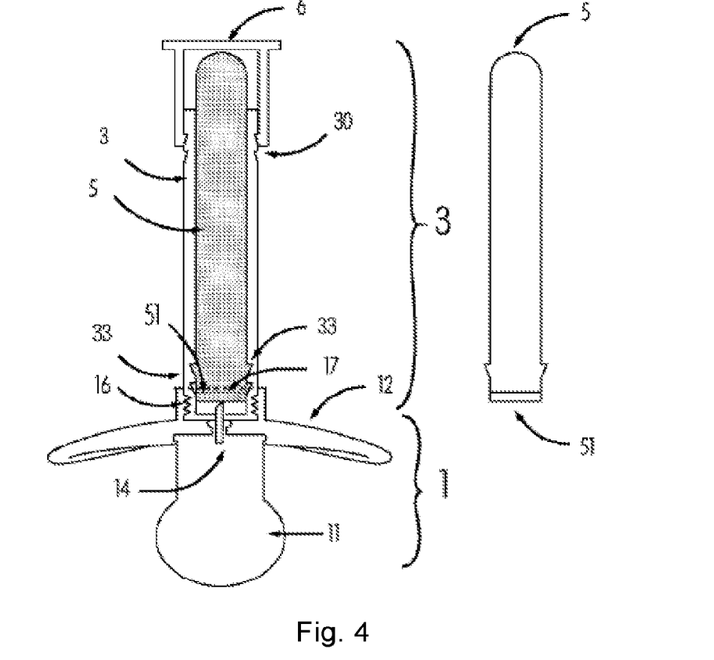
FIG. 4 shows a schematic drawing of an embodiment specifically suited for proving saliva collection away from professional health care. In this embodiment an evacuated sealed sample container (5) is integrated into a guiding member (3) restricted with a cap (6).
Figure 5:
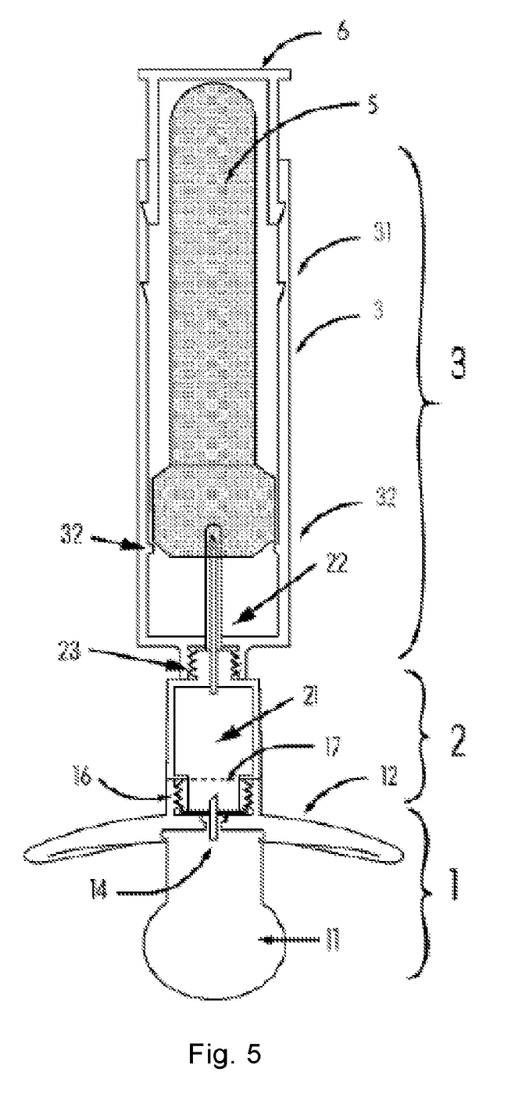
FIG. 5 shows a schematic drawing of a further embodiment adapted for the collection of saliva away from professional health care also comprising a coupling member (2) which may contain a liquid comprising e.g. additives designed for stabilising, preserving and/or analysing the saliva.
Figure 6A:
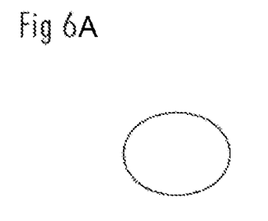
FIGS. 6A-6D show several views of a flexible intra oral member (11).
Figure 6B:
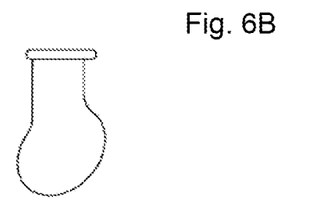
Figure 6C:
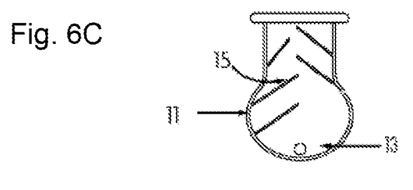
Figure 6D:
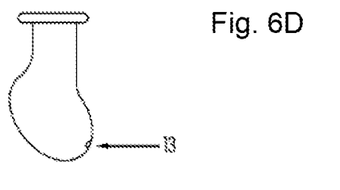

According to yet a further aspect which can be applied to all embodiments of the devices, the sealed evacuated sample container (5) is essentially encapsulated, or fully encapsulated, by an axially moveably cap (6) which engages with the guiding member (2) or the rigid member (12) of the collecting member (1), or directly with the collecting member (1). This aspect of the invention is specifically suited for performing the collection of oral fluids and optional testing at home without further support by medically trained persons such as doctors and nurses. FIGS. 4 and 5 depict examples of devices incorporating a sealed evacuated sample container (5) fully encapsulated by a guiding member (3) and an axially movable cap (6). Suitably, the guiding member comprises features securing the movable cap (6) in two distinct positions. Such positioning features may be present inside (31, 32) or outside (30) the guiding member (3). The guiding member (3) may also comprise means temporarily securing the evacuated sample container from accidentally being penetrated by the needle of the collecting member (1) or the coupling member (2). Such securing means may be protrusions (32) or recesses (33) inside the guiding member (3).

Figure 8:
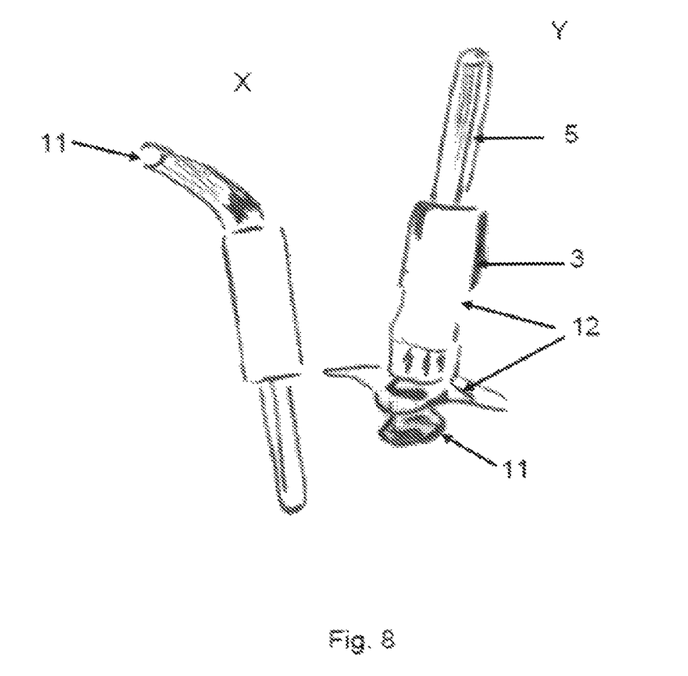
FIGS. 8 and 9 show versions of the concept specifically designed for toddlers (Y) and adults (X, X1, X2).
Figure 9:
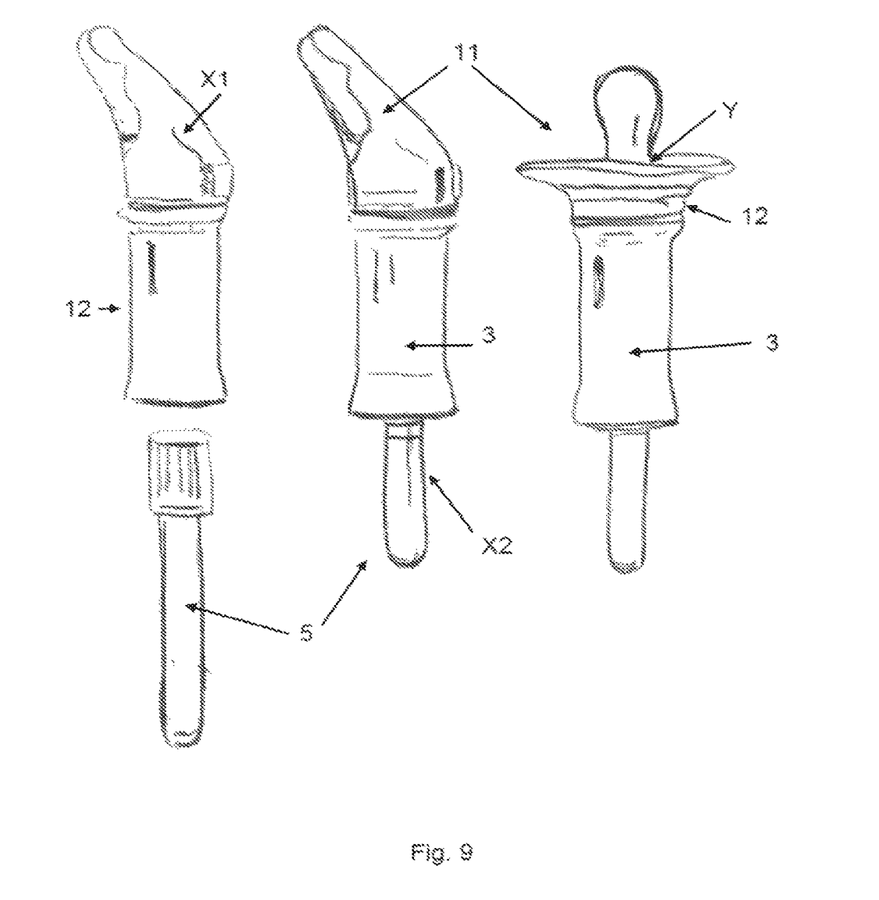

According to embodiment I of the device the rigid member (12), implicitly the collecting member (1), is configured to accommodate an axial movement of a sealed evacuated sample container (5). FIGS. 8 and 9 may present designs of embodiment I where the design of FIG. 8 is primarily intended for children while the design presented in FIG. 9 is an example for adults. The designs of FIGS. 8 and 9 may also represent embodiment II or even III with the individual parts, e.g. guiding member (3) and sealed coupling member (2) already assembled.

According to an embodiment the device may be delivered as a kit of parts comprising the parts identified in embodiments I, II and III as individual parts. Hence, the device of e.g. embodiment II may be provided as a kit (or system) comprising at least the individual parts of a collecting member (1) and a guiding member (3). The device may also be defined as 'a kit' or 'system' such that the device claims are re-worded a kit or a system where the word 'device' is replaced by either 'kit' or 'system'. This system or kit may also contain the sealed evacuated sample container (5). Accordingly, all individual part of the device according to any embodiment may be delivered as one unit. Alternatively, the device is provided as a kit of the individual parts. Sais individual parts are assembled before usage.

According to an embodiment the coupling member (2) may be sealed providing a germ free internal volume. Also, the coupling member may contain a liquid inside the void (21) of the coupling member which comprises additives designed to stabilise, preserve and/or analyse the oral fluids, such as saliva. The sealing of the coupling member is preferably made of a flexible material and may be a material similar to the sealing material of the sealed evacuated sample container, or of a metal or plastic material. Also, the means (22) for penetrating a sealing of the sealed evacuated sample container (5) is sealed with a means (25) serving the purpose of sealing and protecting the user from the penetrating means. According to a further embodiment the coupling member (2) may also comprises a biosensor. The biosensor is herein meant a devices which is capable of facilitating the establishment of a diagnosis using an electric circuitry.

The sealed evacuated sample container (5) may according to an embodiment also comprise a liquid comprising additives with the purpose of stabilise, preserve and/or facilitating the establishment of a diagnosis. This liquid may have the same properties as the liquid in the coupling member. If a sealed evacuated sample container comprises a liquid providing any of the exemplified properties the coupling member may be dispensed with. Thus, a liquid comprising sealed evacuated sample container is suitably combined with a device according to embodiment I and II.

Suitable additives for diagnosis in the liquid, which may be present in the coupling member or the sealed evacuated sample container, may be additives producing a change of colour.

It goes without saying that the invention can be equally practised on humans and animals. When applied on animals the products of the invention might need to be slightly revised yet still constitute embodiments within the gist of the present invention.

One advantage of the inventive concept is the use of evacuated sealed sample containers, and preferably commercially available evacuated sealed sample containers and optionally also guiding members, such as the Vacutainer® system. The evacuated sample container sold under the name Vacutainer® was launched by Becton Dickinson Ltd. in the late '40. The use of sealed evacuated sample containers is since a long time the preferred procedure of collecting e.g. blood samples. Hence, health care provides have well established work processes around the use of evacuated sample containers. As a result the inventive concept can easily be integrated in an established work flow. Furthermore, the concept also provides a convenient and cost effective alternative to invasive sample collection (e.g. blood sampling). Additionally, the concept is also very beneficial for sample collection away from the professional health care. Specifically one aspect of the invention related to an integrated device also comprising the sealed evacuated sample container is attractive for sample collection away from professional health care.

By using an intra oral collecting member the concept is particularly suited for collecting oral fluids from toddlers, young children and elderly persons: Moreover, the concept is an attractive alternative for sample collection from persons with aggravated needle aversion (aka belonephobia).

The collecting member (1) may be defined as being configured for the collection of oral fluids when present in an oral cavity, comprising a flexible intra oral member (11) and a rigid member (12), where the intra oral member (11) comprises at least an opening (13) enabling oral fluids to enter said member and wherein the rigid member (12) comprises means (14) for penetrating a sealing and means (16) for removably securing a coupling member (2) or a guiding member (3,), wherein the collecting member is configured such that a reduced pressure is provided within the oral member when the oral member is within the oral cavity.

The collecting member (1) may also be configured such that any part of the collecting member (1) not being enclosed by the oral cavity is configured for the provision of a reduced pressure. Suitably, the rigid member (12) of the collecting member (1) comprises means which enables a reduction of the pressure within the intra oral member (11) which is formed when the intra oral member (11) gradually retains its uncompressed shape. Such means for the provision of a reduced pressure within the intra oral member (11) may be a penetrable seal which also may have the function of preventing injury from the means for penetrating the sealing, such as a needle.

Furthermore, the rigid member (12) of the collecting member (1) suitably comprises means for penetration of a sealing (14).

According to a further embodiment, the intra oral member (11) comprises essentially one void/cavity alternatively the intra oral member (11) comprises a plurality of cavities being in fluid communication with each other. The intra oral member (11) is suitably configured such that the liquid within the member (11) after oral cavity use easily can be transferred from the member (11) to the sample container (5) by using the vacuum (sub-atmospheric) present in the sealed sample container (5).

The intra oral member (11) is suitably comprised of a resilient material, such as, latex rubber, enclosing one or a plurality voids/volumes, the voids/volumes being in fluidic communication with each other. Suitably, the intra oral member (11) is comprised of a resilient material enclosing essentially one volume.

The resilient material of the intra oral member (11) suitably provides for a reduced pressure when the intra oral member (11) is in the oral cavity. The reduced pressure within the intra oral member (11) is accomplished by compressing the resilient intra oral member (11) between suitable structures within the oral cavity, such as the longue and hard palate. In order to facilitate collection of oral fluids in the collecting member it is preferred that the void does not communicate with the surrounding. i.e. ambient air.

According to an embodiment, the invention encompasses a collecting member (1) configured for the collection of oral fluids when present in an oral cavity, comprising a flexible intra oral member (11) and a rigid member (12), where the intra oral member (11) comprises at least an opening (13) enabling oral fluids to enter said member and wherein the rigid member (12) comprises means (14) for penetrating a sealing and means (16) for removably securing a coupling member (2) or a guiding member (3), wherein parts of the collecting member (1) not being enclosed by the oral cavity, i.e. parts of the collecting member (1) in direct contact with the environment outside the oral cavity (such as parts of rigid member (12), are configured to disable gaseous communication of the volume inside the flexible intra oral member (11) and the environment outside the oral cavity.

According to further aspect of the invention the flexible intra oral member (11) may comprise means which facilitate the transportation of oral fluids in the direction of the coupling member (2) or guiding member (3). Such transportation facilitating means are preferably lamellae of flexible material (15) aggravating the back-flow of oral fluids. The lamellae suitably form an integral part of the flexible intra oral member (11) and are formed of the same material as the flexible intra oral member (11). The flexible intra oral member (11) may also comprise undulations which also serve the purpose of facilitating the transport of oral fluids. The intra oral member (1) comprises a rigid member (12) configured for securing the fixation of the means for penetrating a sealing and accommodating means for removably securing a coupling member or a guiding member (3). Suitably, the means for removably securing further parts may form an integral part of the rigid member. The internal volume of the collecting member restricted by the flexible intra oral member and the rigid member is suitably germ free (sterile) implying that both the opening(s) in the flexible member and the end of the collecting member housing the means for removal securing further parts have a removable sealing. A further feature of the flexible intra oral member (11) is the opening enabling oral fluids to enter the internal volume. In case the opening or openings are positioned within a limited area (opening area) of the flexible intra oral member (11) the position of the opening or openings is somewhat correlated to the rate of accumulation of saliva within the internal volume. For a design of the flexible intra oral member (11) configured for a human oral cavity it is preferred to have the opening area facing towards the upper part of the mouth cavity such as towards the palate. The palate is configured with a hard and soft palate. Suitably the opening area of the flexible intra oral member (11) is located such that the opening(s) is faced towards the palate, preferably hard palate. Depending on use the opening of the flexible intra oral member can have different shapes and sizes. The term opening does not only include one opening but can also relate to a plurality of openings which may be localised in one distinct part of the flexible member or may be more evenly distributed over a larger part of the flexible member. The collecting member (1) is suitably sealed such that the internal volume is sterile. Suitably, the void comprising the means (14) for penetrating a sealing of the rigid member (12) formed by the means (16) for removably securing a coupling member (2) or a guiding member (3), is suitably sealed with a penetrable seal (17).

The sealing not encompassing the means for penetrating the seal of the sample container, such a seals (17) and (24) can be made of a peelable material with a sufficient strength for protecting the user from easily contacting the penetrating means (14), e.g. metal or plastic. Also, the opening (13) of the flexible intra oral member (11) is also sealed with a removable seal.

The means for penetrating a sealing be it a sealing of the coupling member or the evacuated sample container must be sufficiently sharp and rigid to be able to penetrate the sealing without breaking. Typically the penetrating means is hollow and needle-shaped. Suitable materials include polymeric materials and metals.

Figure 2:
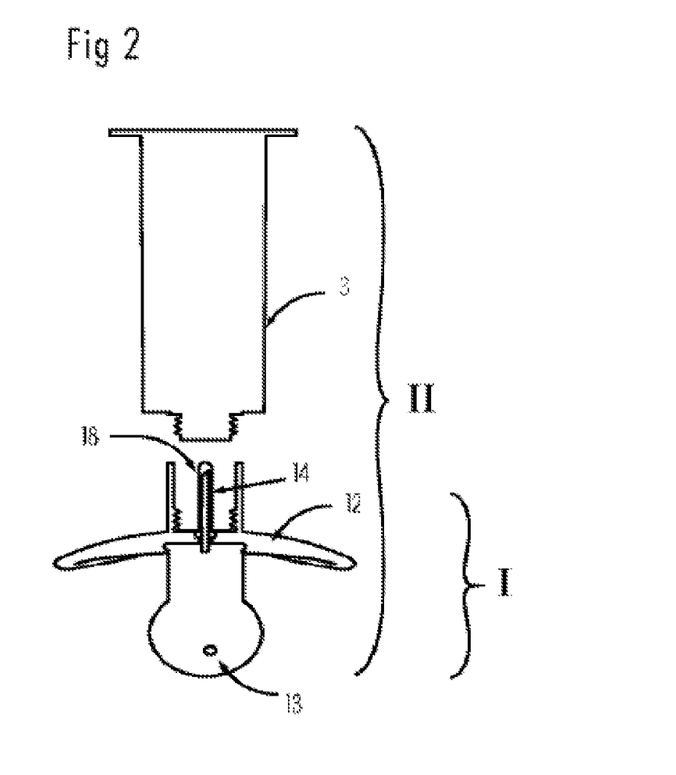
FIG. 2 shows a schematic drawing of an embodiment (II) of the device comprising a collecting member (1) comprising a flexible intra oral member (11) and a rigid member (12) and a guiding member (3). The rigid member (12) also accommodates means (14) for penetration of the seal of the sealed evacuated sample container (5). The void restricted by the flexible intra oral member (11) and the rigid member (12) is sealed (17).
Figure 3:
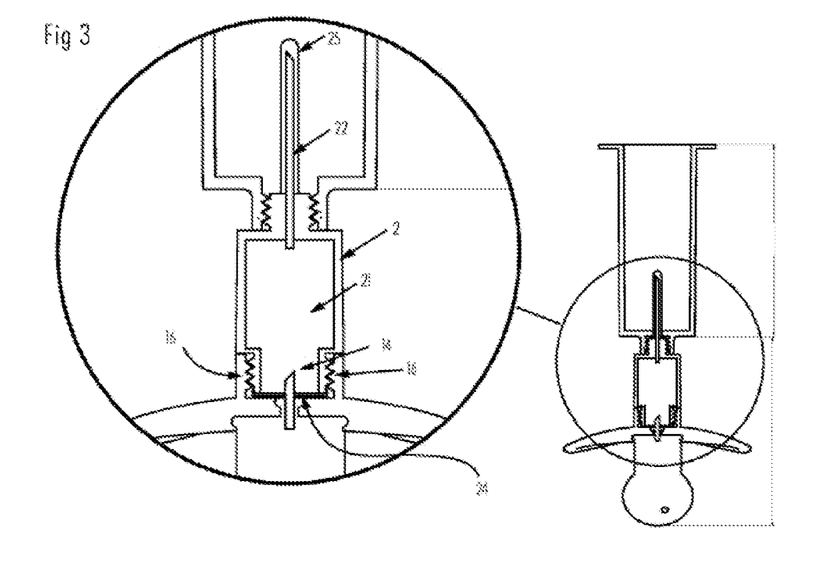
FIG. 3 shows a magnified view of the embodiment (III) in FIG. 1.

FIG. 2 represents an example of the embodiment II. The collecting member (1), resembling a pacifier, contains a flexible intra oral member (11) and a rigid member (12), the flexible intra oral member (11). Also, the flexible member has an opening (13). The collecting member also incorporates threads for the attachment of a guiding member (3) which will accommodate and enable the axial movement of a sealed evacuated sample container (5) (the latter part not depicted). Further to the treads, the collecting member also comprises means for the penetration of the sealing of the sample container which is suitable a hollow needle. The needle has also a sealing which prevents air from entering the cavity (void) through the hollow needle. The collecting member without the guiding member and consequently the sealed evacuated sample container (5), is placed in the oral cavity. By activation of the flexible member oral fluids are collected within the void. When sufficient fluids are collected the member is removed from the oral cavity and the guiding member is attached. Finally, the sealed evacuated sample container (5) is placed inside the guiding member and axially moved in the direction of the collecting member until needle penetrates both the needle seal and specifically the seal of the evacuated sample container. The sub-atmospheric pressure of the sample container is used to suck the oral fluid, e.g. saliva from the void of the collecting member through the hollow needle into the sample container. When the pressure inside the sample container is equal to the ambient pressure, the sample container is removed from the guiding member. The seal of the sample container is of a resilient material which is liquid and essentially air tight after penetration. The sealed sample container can be used for interim storage of the oral fluid. According to an embodiment the sealed evacuated sample container may comprise a fluid, providing one or more functions. The fluid may contain preservatives or components enabling an identification of useful parameters.

Figure 1:
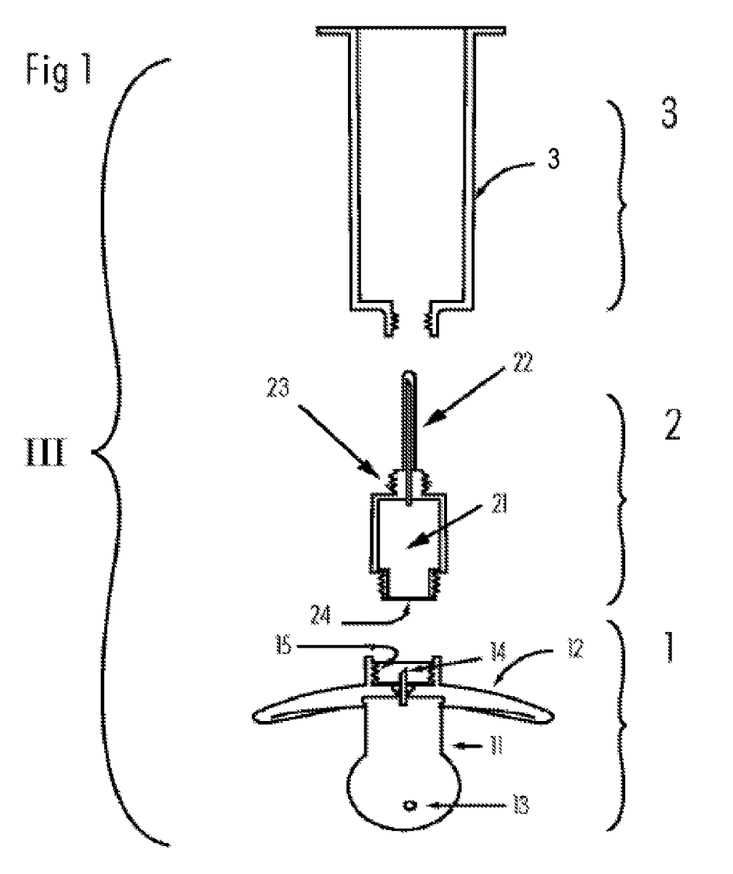
FIG. 1 shows a schematic drawing of an embodiment (III) of the device comprising three main parts being the collecting member (1), coupling member (2), and a guiding member (3).

FIG. 1 depicts an example of embodiment III. This example contains a coupling member (2) which is accommodated between the collecting member (1) and the guiding member (3). All parts are removably secured by threads (16, 23). Usually, the internal volume of the coupling member is filled with a liquid which may contain preservatives, and/or compounds providing the instant characterisation of the oral fluids. The liquid mar for example contain compounds which bring about a color change. If the coupling member (3) contains a liquid said coupling member must be sealed, Further the coupling member (3) must also accommodate a hollow needle (22) which is sealed. Similar to the collecting member II the collecting member has a seal (16) with the same function as in embodiment II. The seal (16) can also serve the function of injury prevention. In this example the hollow needle must have a length capable of breaking the seal (24) of the coupling member (2). The hollow needle secured to the coupling member should have a length capable of penetrating the seal of the evacuated sample container (5). Typically, the collecting member is placed into the oral cavity. After a sufficient amount of oral fluid has been collected in the collecting member the coupling member (2) and the guiding member (3) are connected. Subsequently, the sealed evacuated sample container (5) is introduced into the guiding member and moved axially until the needle of the coupling member has penetrated all seals, i.e. the seal of the needle (25) and the seal of the sample container (51).

FIGS. 4 and 5 depict devices which are suited for collecting saliva away from professional health care. These devices typically contain all parts needed for conducting a saliva sample. The devices may be distributed in a parcel by a postal service to a user. The user positions the intra oral member in the mouth for a period sufficiently filling the internal volume with saliva. In a next step the user pushes the cap in an axial direct such that the seal of the sealed sample container in penetrated by the needle of the coupling member or collecting member. The sub-atmospheric pressure within the sealed evacuated sample container will introduce an amount of saliva correlated to the sub-atmospheric pressure. The user may send the complete device to an entity capable of evaluating the saliva. Alternatively, the user dismantles the devices and sends just the sample compartment comprising the saliva.

The invention claimed is:

1. A device configured for the collection of oral fluids comprising:
   a collecting member, the collecting member comprising a flexible intra oral member and a rigid member, wherein the flexible intra oral member comprises at least one opening, and
   a sealed evacuated sample container, the sealed evacuated sample container comprising a seal
   wherein,
   the collecting member is configured such that, when the flexible intra oral member is present in an oral cavity and when being sucked, a negative pressure inside the flexible intra oral member is provided which enables the collection of oral fluids within the flexible intra oral member; and
   the sealed evacuated sample container is configured to activate when the seal of the sealed evacuated sample container is penetrated by a rigid, hollow structure capable of breaking or penetrating the seal of the sample container so that collected oral fluids are transferred from said flexible intra oral member to said sealed evacuated sample container by activation of a vacuum pressure in the sealed evacuated sample container.

2. A device configured for the collection of oral fluids according to claim 1, wherein
   the rigid member is configured to accommodate an axial movement of the sealed evacuated sample container, and
   the collecting member comprises a means for penetration of the seal of the sealed evacuated sample container.

3. A device configured for the collection of oral fluids according to claim 1, comprising:
   a guiding member configured for accommodating an axial movement of the sealed evacuated sample container, the guiding member configured for enabling removable attachment to the rigid member of the collecting member;
   wherein the collecting member is configured such that the negative pressure inside the flexible intra oral member when present in the oral cavity is provided which enables the collection of oral fluids within the flexible intra oral member and the collecting member comprises means for penetration of the seal of the sealed evacuated sample container.

4. A device configured for the collection of oral fluids according to claim 1, comprising at least:
   a sealed coupling member, comprising an internal volume and a means for penetrating the seal of the sealed evacuated sample container;
   a guiding member configured for accommodating an axial movement of the sealed evacuated sample container; wherein
   the sealed coupling member is configured for enabling removable attachment to the rigid member of the collecting member,
   the guiding member is configured for enabling removable attachment to the sealed coupling member,
   the collecting member is configured such that the negative pressure inside the flexible intra oral member when present in the oral cavity is provided which enables the collection of oral fluids within the flexible intra oral member, and
   the collecting member comprises a means for penetration of a seal of the sealed coupling member.

5. The device according to claim 3, wherein the collecting member, guiding member and a sealed coupling member are provided as one piece, wherein the guiding member accommodates the sealed evacuated sample container, and further comprising an axially movable cap encapsulating the sealed evacuated sample container.

6. The device according to claim 1, wherein the flexible intra oral member comprises a means for facilitating a transportation of oral fluids in a direction to the sealed evacuated sample container.

7. The device according to claim 6, wherein the means for facilitating a transportation of oral fluids are undulations and/or lamellae of flexible material aggravating a back-flow of oral fluids.

8. The device according to claim 1, having an internal volume comprising a liquid.

9. The device according to claim 1, having an internal volume comprising a biosensor.

10. The device according to claim 8, wherein the liquid comprises constituents for preservation and/or constituents enabling an instant preliminary diagnosis.

11. The device according to claim 8, wherein the internal volume is sterile.

12. The device according to claim 1, wherein the collecting member is sealed.

13. A method for collecting oral fluids in the device according to claim 1, the method comprising the steps of:
providing the collecting member configured for the collection of oral fluids when present in the oral cavity, the collecting member comprising the flexible intra oral member and the rigid member, the flexible intra oral member comprising the at least one opening, and the sealed evacuated sample container;
placing the flexible intra oral member in the oral cavity;
collecting the oral fluids in the flexible intra oral member; and
transferring at least part of the oral fluids from the flexible intra oral member into the sealed evacuated sample container by activation of the vacuum pressure in the evacuated sample container.

14. The method according to claim 13, wherein the collecting member is configured such that the negative pressure inside the flexible intra oral member when present in the oral cavity is provided which enables the collection of oral fluids within the flexible intra oral member.

15. The method according to claim 13 wherein the vacuum pressure of the evacuated sample container is activated after a sufficient volume of oral fluid has been collected inside the flexible intra oral member.

16. The method according to claim 13, wherein the sealed evacuated sample container comprising the seal and the sealed evacuated sample container is activated by penetration of the seal.

17. The method according to claim 16, wherein the seal is penetrated by an axial movement of the sealed evacuated sample container.

18. The method according to claim 13, wherein the flexible intra oral member comprises a means for facilitating a transportation of oral fluids in a direction to the sample container.

19. The method according to claim 18, wherein the means for facilitating a transportation of oral fluids are undulations and/or lamellae of flexible material aggravating a back-flow of oral fluids.

* * * * *